United States Patent
Leleu

(10) Patent No.: US 12,357,743 B2
(45) Date of Patent: Jul. 15, 2025

(54) LIGHTWEIGHT POWERED HANDPIECE FOR A LIPOSUCTION DEVICE AND MEDICAL DEVICE COMPRISING SAME

(71) Applicant: PLASCERE, Bourlon (FR)

(72) Inventor: David Leleu, Bourlon (FR)

(73) Assignee: PLASCERE, Bourlon (FR)

( * ) Notice: Subject to any disclaimer, the term of this patent is extended or adjusted under 35 U.S.C. 154(b) by 394 days.

(21) Appl. No.: 17/792,781

(22) PCT Filed: Jan. 17, 2020

(86) PCT No.: PCT/IB2020/000088
§ 371 (c)(1),
(2) Date: Jul. 14, 2022

(87) PCT Pub. No.: WO2021/144602
PCT Pub. Date: Jul. 22, 2021

(65) Prior Publication Data
US 2023/0040313 A1    Feb. 9, 2023

(51) Int. Cl.
*A61M 1/00*    (2006.01)

(52) U.S. Cl.
CPC ............... *A61M 1/76* (2021.05); *A61M 1/89* (2021.05)

(58) Field of Classification Search
CPC .......... A61M 1/76; A61M 1/84; A61M 1/842; A61M 1/89; A61M 2205/10; A61M 2205/106; A61B 2217/002; A61B 2217/005; A61B 17/32; A61B 17/320016–320032; A61B 2017/320024–320032; A61B 17/142; A61B 2018/0019; A61B 2018/00196; A61B 2018/00464
See application file for complete search history.

(56) References Cited

U.S. PATENT DOCUMENTS

| | | | | |
|---|---|---|---|---|
| 4,735,604 A | * | 4/1988 | Watmough | A61B 17/22012 604/35 |
| 5,112,302 A | | 5/1992 | Cucin | |

(Continued)

FOREIGN PATENT DOCUMENTS

WO    WO-2014043475 A1 *    3/2014    .......... A61M 1/0064

OTHER PUBLICATIONS

Int'l. Search Report for PCT/IB2020/000088, dated Nov. 16, 2020.

*Primary Examiner* — Nicholas J. Weiss
*Assistant Examiner* — Linnae E. Raymond
(74) *Attorney, Agent, or Firm* — MaxGoLaw PLLC

(57) ABSTRACT

A powered handpiece for imparting to a cannula of a medical device a reciprocal movement of amplitude ($\Delta x$) along a longitudinal axis (X) is provided. A housing (1) at least partially encloses a hollow tube (2) extending along the longitudinal axis (X) between an inlet end (2$i$) and an outlet end (2$o$), the inlet end (2$i$) being configured for coaxially coupling the hollow tube (2) to a hollow cannula (10). A ring (3) rigidly is coupled to the hollow tube (2) and has an opening (3$o$) defined on a plane (X, Y), having a length, L, Y$\perp$X. A cam (4) mounted on a rotation axle (4$r$) parallel to a second transverse axis (Z) normal to the plane (X, Y) (i.e., X$\perp$Y$\perp$Z), offset from a centroid (C) of the cam on the plane (X, Y) by a distance ($\delta P$), and set at a fixed position relative to the housing (1), the cam being engaged in the opening (3$o$).

17 Claims, 6 Drawing Sheets

(56) References Cited

U.S. PATENT DOCUMENTS

| | | | | |
|---|---|---|---|---|
| 5,224,944 | A | * | 7/1993 | Elliott .................... A61M 1/84 606/49 |
| 6,156,049 | A | | 12/2000 | Lovato et al. |
| 6,761,701 | B2 | * | 7/2004 | Cucin .............. A61B 17/32002 604/35 |
| 8,702,738 | B2 | * | 4/2014 | Mark ............... A61B 17/32002 606/177 |
| 8,888,803 | B2 | | 11/2014 | Mark |
| 2013/0006225 | A1 | * | 1/2013 | Cucin ................ A61B 10/0283 604/542 |
| 2018/0200141 | A1 | * | 7/2018 | Wersland ............. A61H 23/006 |

* cited by examiner

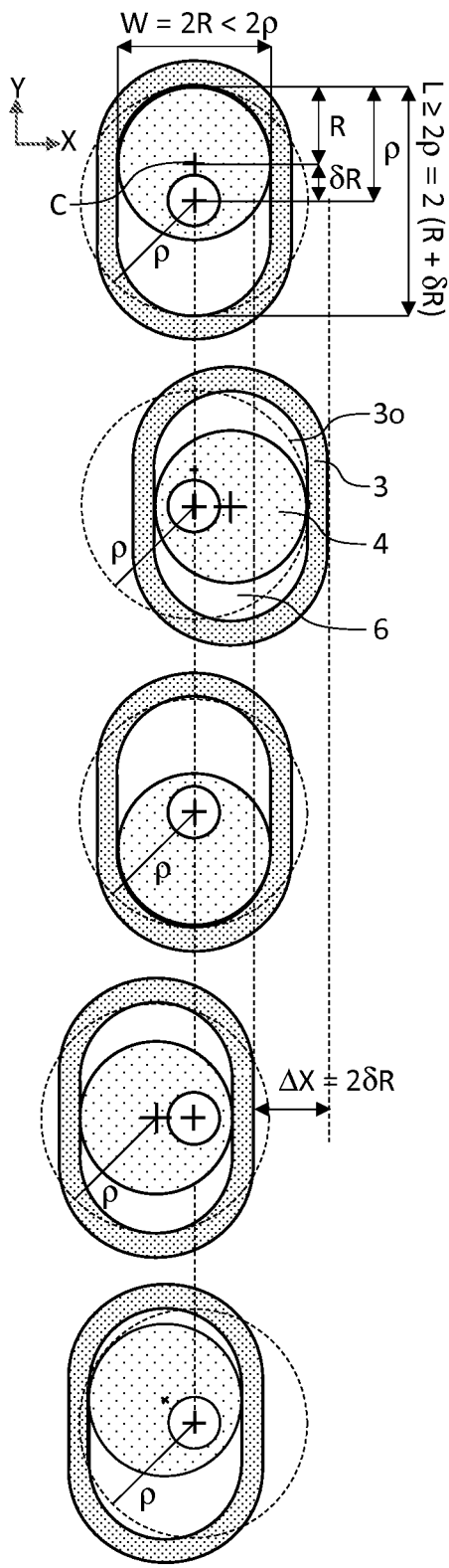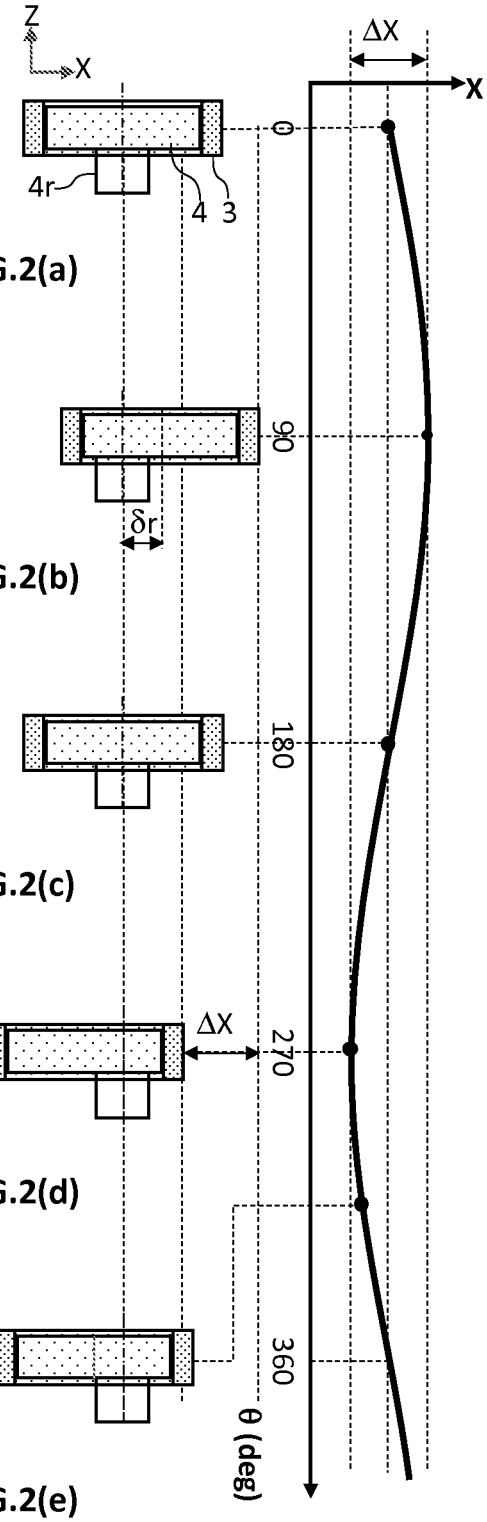
FIG.2(a)
FIG.2(b)
FIG.2(c)
FIG.2(d)
FIG.2(e)

LIGHTWEIGHT POWERED HANDPIECE FOR A LIPOSUCTION DEVICE AND MEDICAL DEVICE COMPRISING SAME

TECHNICAL FIELD

The present invention concerns a liposuction device for extracting adipose tissue from a body of a patient. In particular, it concerns a powered handpiece for such liposuction devices, which is very light, and so cheap that it can be dispensable, requiring no difficult and expensive sterilization operation between uses. In one embodiment, all the components of the powered handpiece can be made of a single polymer family with a possible exception of a few metallic inserts, which facilitates recycling of a disposable powered handpiece.

BACKGROUND OF THE INVENTION

Liposuction devices comprising a long, hollow cannula coupled to a handpiece, with one or more openings at or adjacent to a free end of the cannula are known in the art. The lumen is in fluid communication with a hollow tube and with a vacuum pump for driving the extraction of the adipose tissue, when the free end of the cannula is inserted within the adipose tissue to be treated.

Liposuction devices with a mechanical assistance have been developed for assisting the practitioner during a liposuction operation. The liposuction device comprises a handpiece provided with a mechanical drive for producing and transmitting a reciprocating movement to the cannula. The reciprocating movement was shown to greatly facilitate extraction of adipose tissue. In WO9844966 and in WO2017194386, It was described that the nutation movement of the free end of a cannula in contact with adipose tissues gently disrupts the integrity thereof and facilitates the suction of the disrupted adipose tissue into the cannula. WO2014033209 lists some of the major parameters required for obtaining or not a nutation movement of the free end of a cannula driven along a reciprocal translating movement along a longitudinal direction (X).

The reciprocating translating movement, with or without nutation, is driven by a reciprocating mechanism. Several powered liposuction devices have been commercialized with success, comprising a pneumatic reciprocating device, because it is easier to slow down the movement at the end of the forward and backward apices of the cannula reciprocating movement. For example, each of WO9844966, U.S. Pat. Nos. 6,494,876, 5,911,700, WO2014033209 describes a powered handpiece for a liposuction device comprising a pneumatic reciprocating mechanism. A pneumatic reciprocating mechanism, however, requires a connection to a source of pressurized gas. Tubes must therefore be sealingly coupled to the handpiece for allowing pressurized gas to enter and exit the reciprocal mechanism, which is (1) expensive to produce, (2) heavy, and (3) cumbersome for the practitioner who must handle the handpiece with at least two gas hoses and one flexible tube for the extraction of adipose tissue all coupled to the handpiece.

Powered handpieces for a liposuction device provided with an electrical motor have also been described. For example, WO2017194386 describes a linear electric motor provided with magnets aligned along the trajectory of a reciprocating member. Alternatively, reciprocating mechanisms using an electrical motor driving a rotation movement which is to be transformed into a linear movement can also be used. A first mechanism is described e.g., in U.S. Pat. Nos. 6,494,876, and 5,112,302 and, in the field of devices for cutting tissues, U.S. Pat. No. 6,156,049, wherein the rotary motion of a rotary device driven by an electrical motor is converted into a reciprocating translation motion by pivotally coupling thereto a crankshaft. This mechanism is similar to the one used with steam train engines for rotating the wheels from a linear movement. This solution requires the crankshaft to be pivotally coupled at one end to the rotary device and at the other end to a reciprocating member. Reliable hinge-couplings are difficult to obtain at a low production cost.

U.S. Pat. No. 4,932,935 proposes different embodiments for using a rack and pinion mechanism driven by an electric motor. In the field of devices for cutting tissues wherein an inner cannula reciprocates within an outer cannula, U.S. Pat. No. 8,888,803 describes a longitudinal cam, comprising an elongated pin provided with a groove forming an angle with the longitudinal axis of the pin. A bearing is coupled to the groove, and the rotation of the elongated pin drives the reciprocating translation of the bearing. This solution though apparently simple, is not easy to implement since the bearing must be inserted within the groove, allowing the rotation of the pin relative to the bearing to avoid noise, heat generation, and wear. A ball bearing is described in this document, which increases both the weight and cost of the handpiece.

In many cases, the powered handpieces are quite expensive pieces of equipment which are used repeatedly with new cannulas. They need be sterilized at regular intervals, generally after each use. Sterilizing a powered handpiece is not easy, because the various components thereof, including the driving motor do not support the sterilization conditions of many sterilization techniques (temperature, chemicals, etc.). Powered handpieces are generally quite heavy, which has a tiring effect on the hand of the practitioner after a prolonged handling.

It can be seen from the foregoing discussion that many reciprocating mechanisms have been described in the field of liposuction device, as well as in the neighbouring field of tissue cutting devices. None, however, combines a low cost, low weight, and no need of sterilizing the powered handpiece after use. The present invention proposes a powered handpiece for a liposuction device that combines all these features. These and other advantages of the present invention are presented in continuation.

SUMMARY OF THE INVENTION

The present invention is defined in the appended independent claims. Preferred embodiments are defined in the dependent claims. In particular, the present invention concerns a powered handpiece for imparting to a cannula of a medical device a reciprocal movement of amplitude ($\Delta x$) along a longitudinal axis (X), the powered handpiece comprising a housing (1) at least partially enclosing, (a) a hollow tube (2) extending along the longitudinal axis (X) between an inlet end (2$i$) and an outlet end (2$o$), configured for translating back and forth along the longitudinal axis (X) by a distance ($\Delta X$) relative to the housing (1), the inlet end (2$i$) being configured for coaxially coupling the hollow tube (2) to a hollow cannula (10), (b) a ring (3) rigidly coupled to the hollow tube (2) and comprising an opening (3$o$) defined on a plane (X, Y), having a length, L, measured along a first transverse axis (Y) and a width, W, measured along the longitudinal axis (X), wherein Y$\perp$X, (c) a cam (4) mounted on a rotation axle (4$r$) parallel to a second transverse axis (Z) normal to the plane (X, Y) (i.e., X$\perp$Y$\perp$Z), offset from a centroid (C) of the cam on the plane (X, Y) by a distance (δR), and set at a fixed position relative to the housing (1), the cam being engaged in the opening (3o), wherein upon rotation about the rotation axle, the cam is configured for rotating within the ring and defining a largest radius of rotation (ρ) defined on the plane (X, Y), and wherein the largest radius of rotation (ρ) is not more than half the length, L, of the opening (ρ<½ L) and is larger than the width, W, of the opening, wherein the rotation of the cam (4) engaged in the opening (3o) of the ring (3) drives a reciprocal translation of the hollow tube (2) back and forth along the longitudinal axis (X) by the distance (ΔX) relative to the housing.

In an embodiment of the present invention, the powered handpiece comprises a transmission system for transforming a rotation about a first rotation axis transverse to the second longitudinal axis (Z) driven by a motor into a rotation about a second rotation axis parallel to the second transverse axis (Z) driving the rotation of the cam about the rotation axle, wherein the first rotation axis is preferably parallel to the longitudinal axis (X). For example, the transmission system can be selected among, skew gears comprising a first gear rigidly mounted on the rotation axle, and a second gear configured for rotating about the first rotation axis and mechanically interacting with the first gear for driving the rotation of the first gear about the rotation axle, or the first gear engaged with a worm gear rotating about the first rotation axis, or a cardan joint, preferably a homokinetic joint, more preferably a double-cardan joint.

The powered handpiece can comprise an outlet tube rigidly fixed to the housing, positioned coaxially to the hollow tube, with a proximal end facing without contact the outlet end of the hollow tube, and with a distal end extending out of the housing. A sealing component is provided for sealing from an outer atmosphere a space comprised between the outlet end of the hollow tube and the proximal end of the outlet tube, allowing for the back and forth translation of the hollow tube relative to the housing and to the outlet tube. For example, the sealing component can be selected among, a chamber rigidly fixed relative to the outlet tube and comprising dynamic sealing elements sealing an interface between the hollow tube and a wall of the chamber during the back and forth translation of the hollow tube relative to the housing, a bellow sealed to or integral with the hollow tube and the outlet tube, or a sheath made of a flexible material sealed to or integral with the hollow tube and the outlet tube, preferably the flexible material is an elastomeric material.

In an embodiment, the powered handpiece is disposable. It is supplied in a sterile packaging and is designed for a single use. To prevent a user from using the powered handpiece more than once, the powered handpiece can comprise at least one component essential for the use of the powered handpiece for liposuction of adipose tissue, which is degraded at a temperature of not more than 60° C., preferably above 100° C. This way, the powered handpiece cannot be used after a sterilization operation at a temperature above 60° C. or above 100° C.

The present invention also concerns a kit of parts for liposuction of adipose tissue comprising, (a) a powered handpiece as discussed supra,
(b) a hollow cannula comprising a lumen and having a coupling end configured for being coupled to the inlet end of the hollow tube, and a free end,
(c) a motor) mechanically coupled to the cam for driving the rotation of the cam about the rotation axle,
(d) a vacuum pump configured for being coupled via a flexible tube in fluid communication with the outlet end) of the hollow tube, preferably via the distal end of the outlet tube, and for creating a vacuum in the lumen of the cannula sufficient for drawing adipose tissue out of a location of a body
(e) a collecting vessel configured for collecting adipose tissue extracted through the cannula and for being sealingly coupled to the vacuum pump and including an opening for receiving a downstream end of the flexible tube.

It is preferred that the motor is separate from the housing and is directly or indirectly mechanically coupled to the cam via a cable configured for transmitting a rotational torque for driving the rotation of the cam about the rotation axle. The motor can be an electric motor, a pneumatic motor, or a hydraulic motor.

The present invention also concerns a medical device for removing tissues from a body. The medical device is preferably a device for liposuction. The medical device comprises, a powered handpiece as discussed supra,
a hollow cannula extending between a coupled end and a free end, the coupled end being fixed to the inlet end of the hollow tube, such that the hollow cannula extends along the longitudinal axis (X) with the free end being located outside the powered handpiece, and
a motor configured for rotating the cam about the rotation axle and thus driving the back-and-forth translation of both hollow tube and hollow cannula along the longitudinal axis (X).

For liposuction applications, it is preferred that the medical device be configured for imparting a nutational movement to the free end of the hollow cannula when the hollow tube translates back-and-forth along the longitudinal axis (Z).

In alternative applications, the medical device can comprise an outer cannula fixed relative to the housing, and wherein the cannula is an inner cannula enclosed in the outer cannula and configured for reciprocating along the longitudinal axis (X) relative to the outer cannula. Both inner and outer cannulas comprise one or more openings adjacent to the free end of the cannulas. The relative movement of the inner cannula and outer cannula alternatively drives in and out of registry the one or more openings of the inner and outer cannulas, thus cutting any tissue drawn through a pair of corresponding openings of the cannulas.

The motor is preferably separate from the housing and is directly or indirectly mechanically coupled to the cam via a cable configured for transmitting a rotational torque for driving the rotation of the cam about the rotation axle.

BRIEF DESCRIPTION OF THE FIGURES

For a fuller understanding of the nature of the present invention, reference is made to the following detailed description taken in conjunction with the accompanying drawings in which:

FIG. 2: shows the reciprocal movement (right-hand side curve) of a cannula driven by the rotation of the cam within the ring opening at different rotational angles (a) to (e) (left-hand side: top views; middle: side views).

DETAILED DESCRIPTION OF THE INVENTION

Figure 1A:
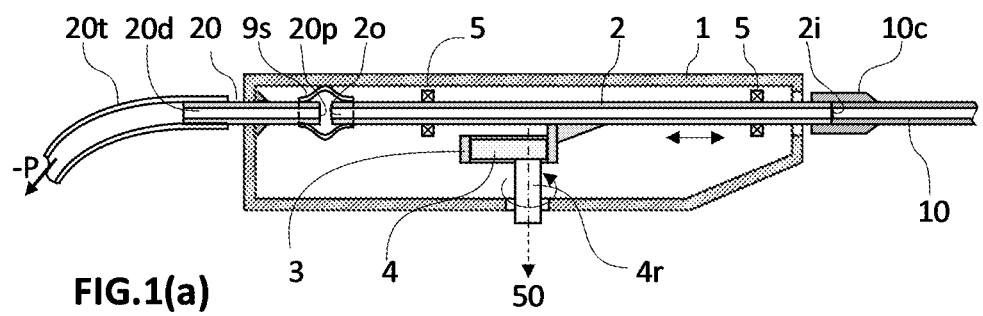
FIG. 1: shows several embodiments (a) to (d) of powered handpieces according to the present invention, with a cannula and a flexible tube coupled thereto.

The present invention concerns a powered handpiece for a liposuction device. It also concerns a kit of parts and a medical device for removing tissue from a body. In a preferred embodiment, the medical device of the present invention comprises all the elements of the kit of parts, assembled together such as to bring in fluid communication the various elements with one another in an appropriate way.

The powered handpiece of the present invention can be configured for being a disposable handpiece, which is to be dispensed of after one use. This approach eliminates the difficult operation of sterilization of the handpiece after each use but increases the volume of waste thus generated. For these reasons, the powered handpieces must be cheap to produce while maintaining a high level of reliability and accuracy and, at the same time, they are preferably easy to recycle. Production costs are reduced by simplifying the design of the actuation mechanism for transmitting a reciprocal movement to the cannula and by dissociating the motor from the handpiece. Most or all components can be made of a polymer of the same family, preferably a thermoplastic material such as a polyaryl ether ketone including PEEK, PEKK, PEKKEK, PEK, or PEKK, a polyolefin (e.g., PE, PP, HDPE), a polyamide (e.g., PA6, PA6.6, PA12), a polyester (e.g., PET, PEN), a polyurethane, and copolymers thereof. This facilitates recycling of a spent handpiece.

To prevent misuse of a disposable handpiece by using it several times like a conventional powered handpiece, at least one component essential for the use of the powered handpiece for liposuction of adipose tissue can be made of a material which degrades at a temperature of not more than 60° C., preferably above 100° C., such that the powered handpiece cannot be used after a sterilization operation at a temperature above 60° C. or above 100° C.

The components of a powered handpiece according to the present invention, disposable or not, are discussed in the following.

Powered Handpiece—Reciprocating Mechanism

The powered handpiece of the present invention is configured for imparting to a cannula of a medical device a reciprocal movement of amplitude, $\Delta X$, along a longitudinal axis (X). As shown In FIGS. 1(a) to 1(d), the powered handpiece comprises a housing (1) at least partially enclosing the following elements.

A hollow tube (2) extending along the longitudinal axis (X) between an inlet end (2i) and an outlet end (2o), is configured for translating back and forth along the longitudinal axis (X) by a distance, $\Delta X$, relative to the housing (1). The inlet end (2i) is configured for coaxially coupling the hollow tube (2) to a hollow cannula (10).

A ring (3) is rigidly coupled to the hollow tube (2) and comprises an opening (3o) defined on a plane (X, Y). The opening (3o) has a length, L, measured along a first transverse axis (Y) and a width, W, measured along the longitudinal axis (X), wherein $Y \perp X$, A cam (4) is mounted on a rotation axle (4r) parallel to a second transverse axis (Z) normal to the plane (X, Y) (i.e., $X \perp Y \perp Z$), offset from a centroid (C) of the cam on the plane (X, Y) by a distance, $\delta R$, and set at a fixed position relative to the housing (1). The cam is engaged in the opening (3o), wherein upon rotation about the rotation axle, the cam is configured for rotating within the ring and defining a largest radius of rotation ($\rho$) defined on the plane (X, Y), wherein the largest radius of rotation, $\rho$, is not more than half the length, L, of the opening ($\rho \leq \frac{1}{2} L$) and is larger than the width, W, of the opening, wherein the difference between twice the largest radius of rotation, $\rho$, and the width, W, of the opening is equal to the distance, $\Delta X$, (i.e., $2\rho - W = \Delta X$).

FIGS. 3(a) to 3(d) show the same rings and cams configurations as illustrated in FIGS. 2(a) to 2(e), which are integrated in a medical device comprising a handpiece comprising a housing (1), a cannula (10) and a flexible tube (20t). As illustrated in FIGS. 2 and 3, the drive of the reciprocating translation of a cannula rigidly fixed to the hollow tube (2) is made possible by the rotation of the cam (4) engaged in the opening (3o) of the ring (3) which is itself rigidly fixed to the hollow tube. Translating the ring along the longitudinal axis (X) therefore inevitably drives a cannula fixed to the hollow tube along the same reciprocal trajectory. As shown in detail in FIGS. 2(a) to 2(e) and 3(a) to 3(d), the cam (4) is at a start position, defined in FIG. 2(a) as an angular position of 0° corresponding to the ring and therefore the cannula being at mid-position of their reciprocating translations of amplitude $\Delta X$. By rotation of the cam by an angle $\theta = 90°$, as shown in FIG. 2(b), the cam pushes the ring forward by a distance $\frac{1}{2} \Delta X$, which drives the cannula to its forward apex position. By a further rotation of 90° (i.e., 180° compared with the start position), as shown in FIG. 2(c), the ring is brought back to its start position, thus driving the cannula back to the mid-position it had at the start position. Another rotation of 90°, summing up 270° from the start position, the ring is pushed backwards, driving the cannula to its backward apex position of its reciprocal translation. A further rotation in the same direction pushes the ring forward again, until it reaches it start position after completing a 360° rotation (cf. FIG. 2(e) and ($\theta$–X) plot on the right-hand side, showing the position X of the ring (or cannula) as a function of rotation angle $\theta$ of the cam).

Since the largest radius of rotation p is not more than half the length, L, of the opening, and is preferably equal to or slightly smaller than half the length, L, the rotation of the cam (4) does not drive any translation of the ring along the first transverse axis (Y) (compare FIGS. 2(a) and 2(c), wherein the ring is never driven transversally by the rotation of the cam. It is clear that the longest segment passing through the axis of the axle (4r) linking two points of a perimeter of the cam (corresponding to a diameter, 2R, of a circular cam) must be equal to or smaller than the width, W, of the ring opening, to allow rotation of the cam within the ring opening. By slightly smaller or slightly larger it is herein meant that there is not more than 5%, preferably not more than 3% difference between two values.

Figure 5:
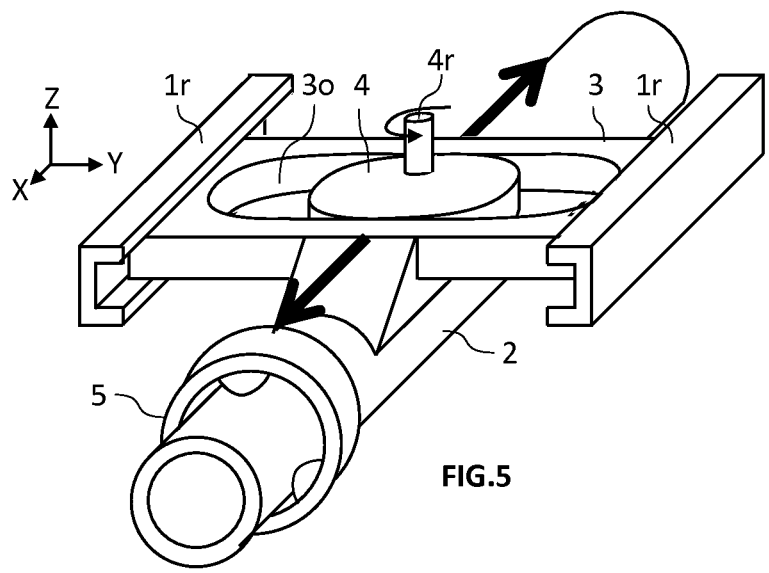
FIG. 5: shows an embodiment comprising rails for guiding the ring along the longitudinal axis.

In a preferred embodiment illustrated in FIG. 5, the housing may comprise a pair of rails (1r), e.g., C-shaped profiles, rigidly fixed to the housing (1) and extending along the longitudinal axis (X) on either side of the ring (3) The rails (1r) are configured for guiding the ring (3) and for preventing the ring from moving sideways along the first transverse axis (Y), and thus allowing the movements of the ring solely along the longitudinal axis (X). Regardless of whether the housing comprises rails (1r) or not, the hollow tube (2) is preferably supported by bearings (5) to guide the reciprocal translation thereof along the longitudinal axis (X). Traditional ball bearings can be used, but to reduce weight and cost, and enhance recyclability, polymer bearings, readily available on the market are preferred. A simple form of bearing (5) is illustrated in FIG. 5, comprising a ring surrounding the hollow tube (2) with at least three protrusions projecting inwards from an inner surface of the ring, thus supporting the hollow tube at the tips of the protrusions only. This embodiment is interesting as it can be injection moulded in one piece, comprising no mobile parts, and can be made of a same polymer as the housing and all other components enclosed in the housing.

Because the largest radius of rotation (ρ) is larger than the width, W, of the opening measured along the longitudinal axis, the rotation of the cam (4) pushes the ring (3) back and forth imposing a reciprocal movement relative to the housing of amplitude, ΔX.

The cam (4) can be circular as illustrated in FIGS. 2(a)-2(e) and 3(a)-(d) or can have any geometry with a largest length not larger than the width W of the ring opening (3o), wherein the largest length of the cam is defined as the longest straight segment connecting two points of a perimeter of the cam on the plane (X, Y). In a preferred embodiment illustrated in FIGS. 2(a)-2(e) and 3(a)-(d), the cam is circular of diameter, 2R, equal to or slightly lower than the width, W, of the ring opening (3o) to ensure a smooth reciprocal movement of the ring (3) and the cannula (10), as the cam can thus always have a contact at two point with the ring (3). In this embodiment, the largest radius of rotation, ρ, of the circular cam is equal to R+2δR and the amplitude of the reciprocal movement is ΔX=2δR. The largest radius of rotation, ρ, is preferably equal to or slightly lower than half the length L of the ring opening (3o). This allows saving space and reducing the dimensions of the housing.

Figure 6A:
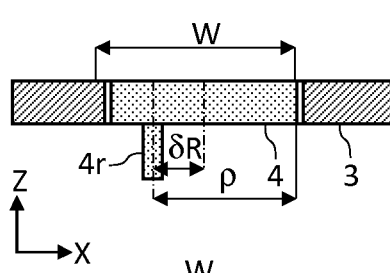
FIG. 6; shows various embodiments (a) to (d) of peripheral edge geometries of the cam and ring opening.
Figure 6A:
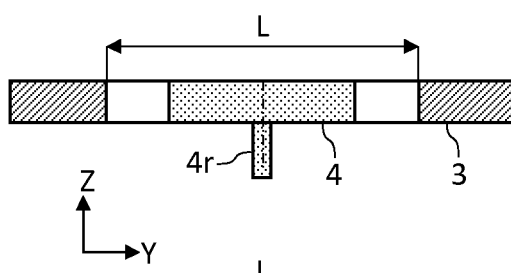
Figure 6B:
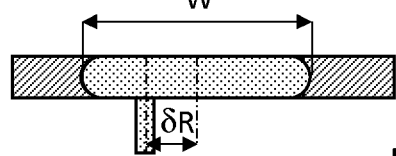
Figure 6B:
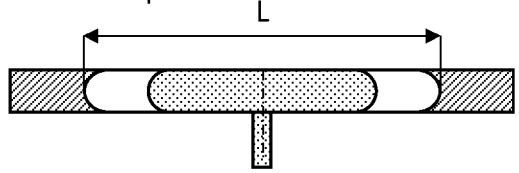
Figure 6C:
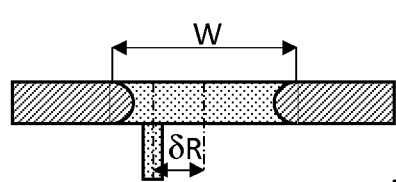
Figure 6C:
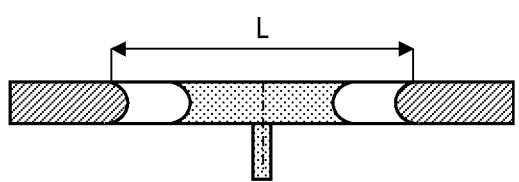
Figure 6D:
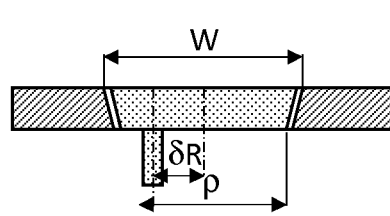
Figure 6D:
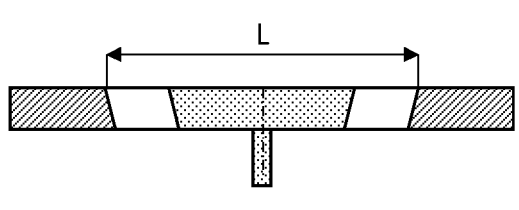

As shown in FIG. 6(a) to (d), the peripheral edge of the cam can be straight, as shown in FIG. 6(a), but can have any other geometry, such as convex as in FIG. 6(b), concave, as shown in FIG. 6(c), trapezoidal as shown in FIG. 6(d). The peripheral edge of the ring opening (3o) must have a complementary geometry allowing a mating of the peripheral edge of the cam. Non-straight peripheral edges of the cam and the ring opening have the advantage that the cam is limited in its movements relative to the ring along the second transverse axis (Z), ensuring a higher stability and reliability of the powered handpiece.

The reciprocating mechanism comprising a cam (4) cooperating with a ring (3) rigidly fixed to a hollow tube (2) described supra transforms the rotational movement of the cam into a reciprocal translating movement of the hollow tube. All the components required for this movement transformation have a simple geometry and are easily produced, e.g., by injection moulding. No hinges or additional joining elements are required, thus greatly simplifying the design and production of the reciprocating mechanism. The rotation of the cam is driven by a motor (50).

Powered Handpiece—Motor Drive (50)

The rotation of the cam (4) about the rotation axle (4r) is driven by a motor axle of the motor (50). The motor (50) is preferably an electric motor, a pneumatic motor or a hydraulic motor. The motor is preferably an electric motor. In a first embodiment illustrated in FIGS. 4(a) and 4(b), the motor (50) is separate from the powered handpiece and configured for mechanically coupling the motor axle to the rotation axle (4r) of the cam (4) such as to drive the rotation of the cam about the rotation axle. In order to allow freedom of movement of the handpiece relative to the motor, the latter is preferably coupled to the rotation axle of the cam by means of a cable (50c) flexible enough for freedom of movements and having a moment of torsion sufficiently high to transmit the rotation torque of the motor axle to the rotation axle (4r) of the cam (4). The cable can be made of metal such as steel, preferably stainless steel, or of a polymer such as a polyamide (e.g., PA6, PA66, PA12, and the like). This embodiment of separating the motor from the powered handpiece has several advantages. First, the powered handpiece is much lighter, thus improving the ergonomics of use for the practitioner, in particular for long operations. Second, it reduces the production cost of the powered handpiece and, third, it improves the recyclability of the powered handpiece as the motor cannot be made of the same polymers as the handpiece and would need be removed from the handpiece prior to recycling the latter.

Figure 4A:
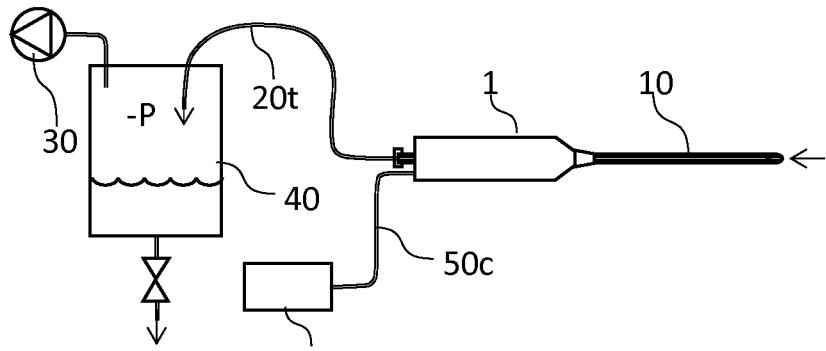
FIG. 4: shows various embodiments (a) to (d) of a medical device according to the present invention for the liposuction.
Figure 4B:
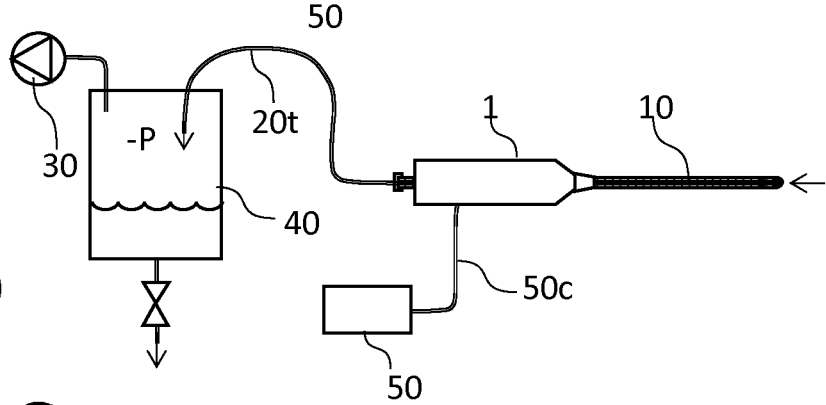
Figure 4C:
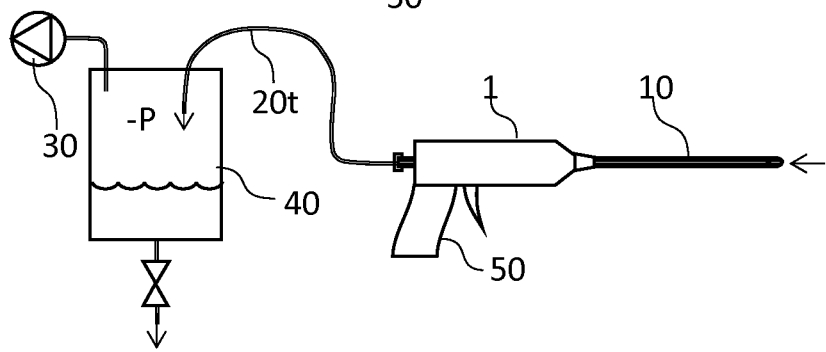
Figure 4D:
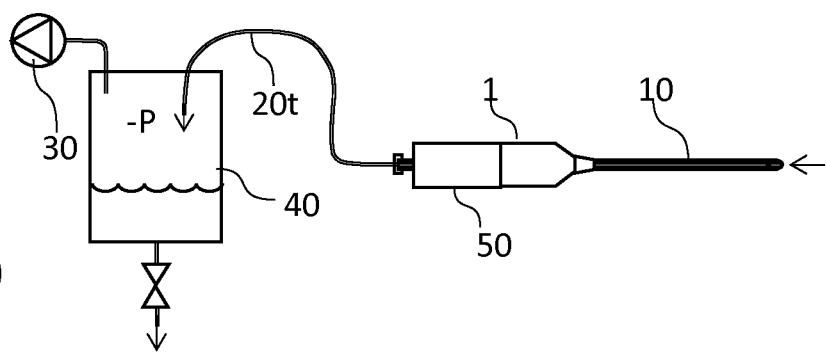

In a second embodiment illustrated in FIGS. 4(c) and 4(d), the motor (50) can be reversibly coupled to the powered handpiece. As shown in FIG. 4(c), the motor can be coupled to the handpiece in or forming a handle thereof in a pistol clip- or grip-like fashion. As shown in FIG. 4(d), the motor can be coupled to a rear portion of the handpiece to form, together with the handpiece, a continuous cylindrical grip. The handpiece is not as light as in the embodiment with a motor remote from the handpiece, but this embodiment is advantageous in that the motor axle can be coupled directly to the rotation axle (4r) and no cable (50c) or any other external connection is required anymore, which would hinder the movements of the practitioner. Production cost and recyclability are also improved, as the same motor can be used with different handpieces, and when a handpiece is worn, the motor can be decoupled from the handpiece and the latter can be recycled easily.

The rotation of the motor axle can be transmitted to the axle of the cam either parallelly, preferably coaxially, or transversally, preferably normal to one another. FIGS. 1(a), 4(b) and 4(c) illustrate embodiments wherein the motor axle or the cable (50c) and the rotation axle (4r) are both parallel to the second transverse axis (Z). If the two axles (or cable (50c) and rotation axle (4r)) are parallel but not coaxial, a mechanical connection is required to transmit the rotation torque from the motor axle or cable (50c) to the rotation axle of the cam, such as gears or a belt. If the two axles (or cable (50c) and rotation axle (4r)) are coaxial, then the coupling can be a rigid rotational coupling which is much simpler and more economic than a gear or a belt. For example, the rigid rotational coupling can be a male-female connection of two mating axle/cable ends having a non-revolution cross-sectional geometry. In the embodiment of FIG. 4(b), the coupling is between a cable (50c) and the rotation axle (4r), and in the embodiment of FIG. 4(c), the coupling is directly between the motor axle and the rotation axle (4r).

FIGS. 1(b) to 1(d), 4(a) and 4(d) illustrate embodiments wherein the motor axle or the cable (50c) and the rotation axle (4r) are transverse, preferably normal to one another. These embodiments require a transmission system for transforming the rotation of the motor axle or cable (50c) about a first rotation axis transverse to the second longitudinal axis (Z) driven by the motor (50) into a rotation about a second rotation axis parallel to the second transverse axis (Z) driving the rotation of the cam about the rotation axle (4r), wherein the first rotation axis is preferably parallel to the longitudinal axis (X). For example, the transmission system can be selected among the following mechanisms.

Figure 1B:
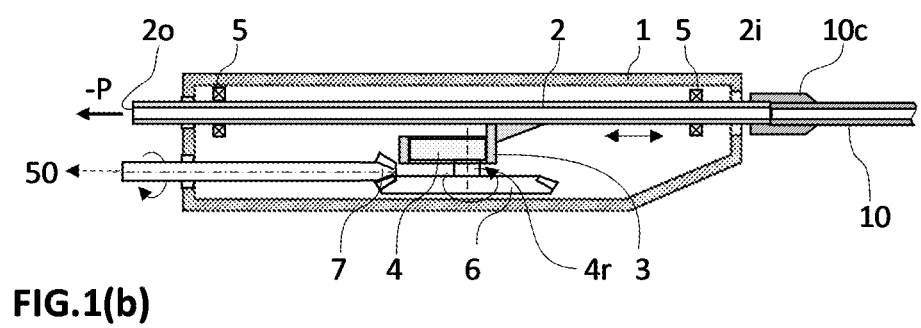
Figure 1C:
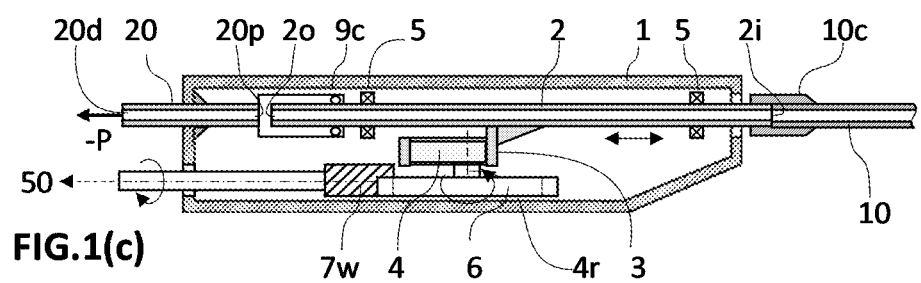

FIG. 1(b) illustrates skew gears comprising a first gear (6) rigidly mounted on the rotation axle (4r), and a second gear (7) configured for rotating about the first rotation axis and mechanically interacting with the first gear for driving the rotation of the first gear about the rotation axle (4r). Alternatively, FIG. 1(c) shows a first gear (6) engaged with a worm gear (7w) rotating about the first rotation axis. Another embodiment (not illustrated) includes the use of a cardan joint, preferably a homokinetic joint, more preferably a double-cardan joint.

Joining Portion (50J) Between Cable (50C) and Rotational Axle (50R, 7R) of Cam (4) or of Second Gear (7)

Figure 7A:
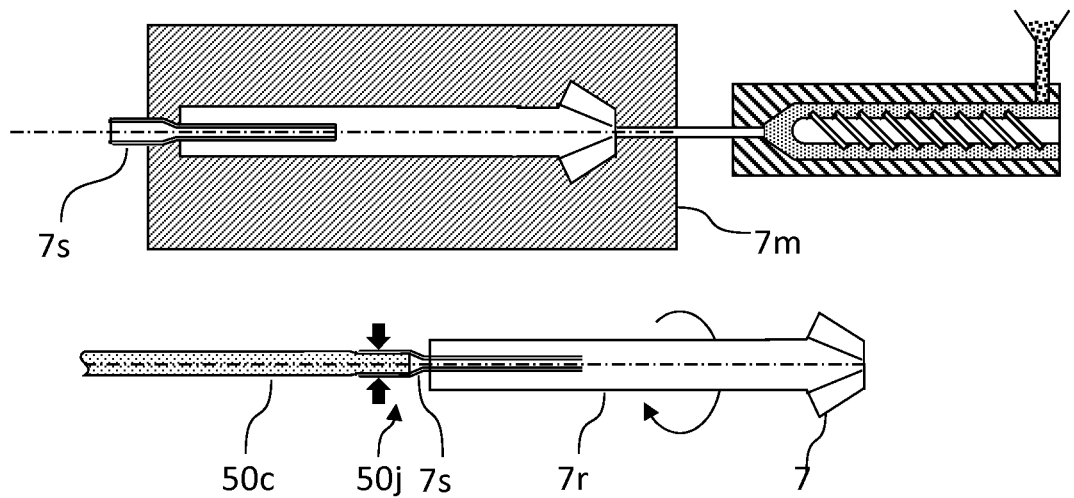
FIG. 7: shows embodiments for joining a cable to a rotational axle of a cam or of a second gear, by (a) swaging, (b) gluing or welding, and (c) over-moulding.
Figure 7B:
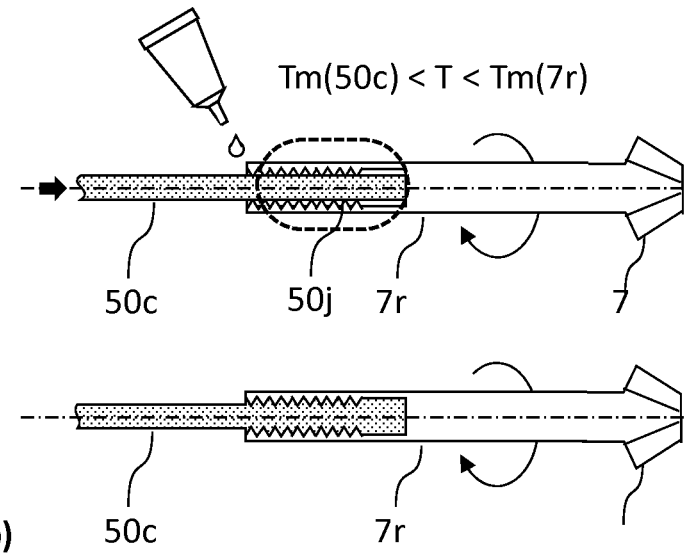
Figure 7C:
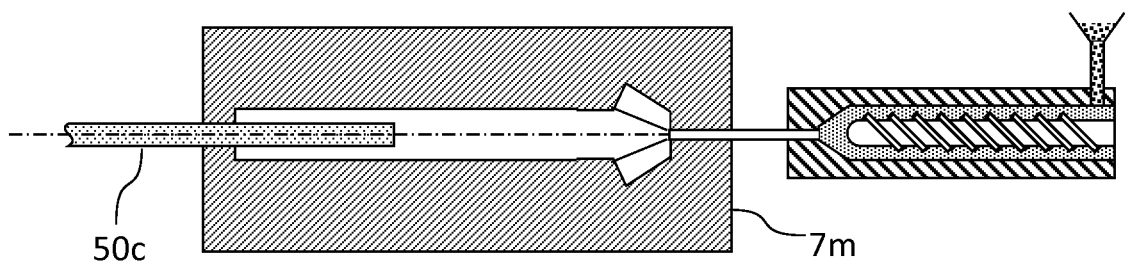

In the embodiment comprising a cable (50c) for transmitting the torque of the motor (50) to the cam (4) or to the second gear (7), the cable can be joined to the rotational axis (4r, 7r) of the cam or of the second gear by different techniques. FIGS. 7(a) to 7(c) illustrate three such techniques for joining a cable (50c) to the rotational axle (7r) of the second gear. It is clear that the same techniques can be applied mutatis mutandis to the rotational axles (4r) of the cam (4).

In FIG. 7(a) the rotational axle (4r, 7r) of the cam (not shown) or of the second gear (7) is coupled to the cable (50c) by means of a swaging tube (7s). The swaging tube (7s) must be made of a material which can be swaged, such as a metal including steel, stainless steel, aluminium, titanium and the like. The rotational axle (4r, 7r) and cam (4) or second gear (7) are preferably made of a polymer as discussed supra and produced by injection moulding in one shot. As illustrated in FIG. 7(a) top illustration, the swaging tube (7s) can be partly inserted into the injection moulding mould (7m) used for forming the rotational axle (with any opening thereof located within the mould previously sealed) and the rotational axle (and cam or second gear) can be over-moulded over the swaging tube, partly embedding it coaxially in the rotational axle (4r 7r) with one end (the sealed one) embedded in the axle and a free end located outside the axle. The free end of the swaging tube (7s) comprises a swaging portion, i.e., an expanded portion, to accommodate a cable (50c) therein. The swaging portion can then be pressed to swage the cable (50c) within the swaging tube (7s), thus forming a joining portion (50j). The swaging tube (7s) can comprise a texture including protrusions or recesses on an outer and/or an inner surface thereof. The texture on the outer surface of the swaging tube anchors it within the rotational axis (4r, 7r) during the over-moulding operation, thus preventing the swaging tube (7s) from rotation or translating relative to the rotational axle. The texture on the inner surface can be advantageous to anchor the cable (50c) within the swaging portion, preventing any rotation and translation of the cable relative to the swaging tube (7s).

In FIG. 7(b), the free end of the rotational axle (4r, 7r) can comprise a lumen. The cable (50c) can be inserted into the lumen and fixed thereto either with an adhesive, or by welding, i.e., by heating the joining portion (50j) above the melting temperature of the cable (50c) and subsequently cooled. The welding process is of course possible only if the melting temperature (Tm(50c)) of the cable (50c) is lower than the melting temperature (Tm(7r)) of the rotational axle (4r, 7r). For example, the rotational axle can be made of PEEK. For example, the cable can be made of polyamide (e.g., PA6, PA66, PA12, and the like). Again, the inner surface of the lumen can be textured to prevent any slippage between the cable and the rotational axle.

As shown in FIG. 7(c), the rotational axle (4r, 7r) and corresponding cam or second gear can be over-moulded over the cable (50c) which is partly inserted in the mould (7m). This solution only applies if the melting temperature (Tm(50c)) is higher than the injection moulding temperature of the polymer used for forming the rotational axle (4r, 50c). For example, the cable (50c) can be made of a poly aryl ketone, such as PEEK, PEKK, PEKKEK, or the like, or of PEI (polyether imide) and the rotational axle can be made of a polyamide or a polyolefin. Again, the surface of the cable near the end inserted in the mould can be textured to create an anchoring effect.

Powered Handpiece—Hollow Tube (2)

The hollow tube (2) is rigidly fixed to the ring (3), so that the reciprocating translation movement of the ring driven by the rotation of the cam (4) is transmitted to the hollow tube (2). The hollow tube (2) has an inlet end (2i) configured for being rigidly fixed to a cannula (10), and an outlet end configured for being coupled in fluid communication with a flexible tube (20t) fluidly coupled to a collecting vessel (40) at a lower pressure for collecting adipose tissue extracted from a body. In use, both inlet and outlet ends (2i, 2o) of the hollow tube oscillate in and out. The flexible tube (20t) can be coupled directly to the outlet end (2o) of the hollow tube as shown in FIG. 1(b). This of course greatly simplifies the design of the handpiece, but this solution is not comfortable for the practitioner since the reciprocating movement of the outlet end (2o) of the hollow tube creates strong oscillations of the flexible tube (20t) which can wobble uncomfortably. It is therefore preferred to provide a system preventing the oscillations of the flexible tube (20t). For example such system can comprise an outlet tube (20) rigidly fixed to the housing (1), positioned coaxially to the hollow tube (2), with a proximal end (20p) located inside the housing and facing without contact the outlet end (2o) of the hollow tube (2), and with a distal end (20d) extending out of the housing. The distal end (20d) of the outlet tube (20) is configured for coupling to the flexible tube (20t). A sealing component (9b, 9c, 9s) is interposed between the hollow tube and the outlet tube for fluidly coupling the oscillating outlet end (2o) of the hollow tube (2) with the static proximal end of the outlet tube (20) while ensuring a continuous fluidic path between the two. Several solutions exist for the sealing component.

Figure 1D:
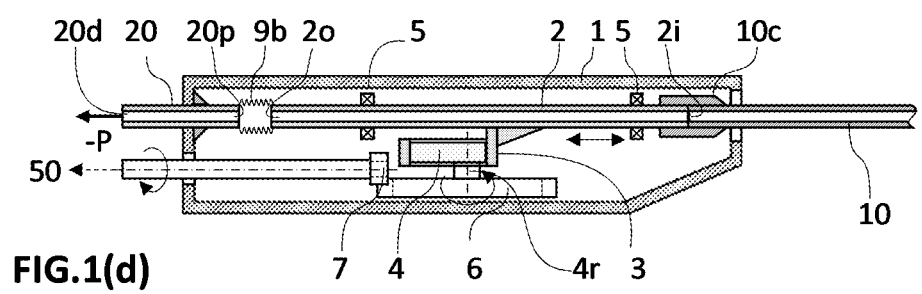
Figures 3A, 3B, 3C, 3D:
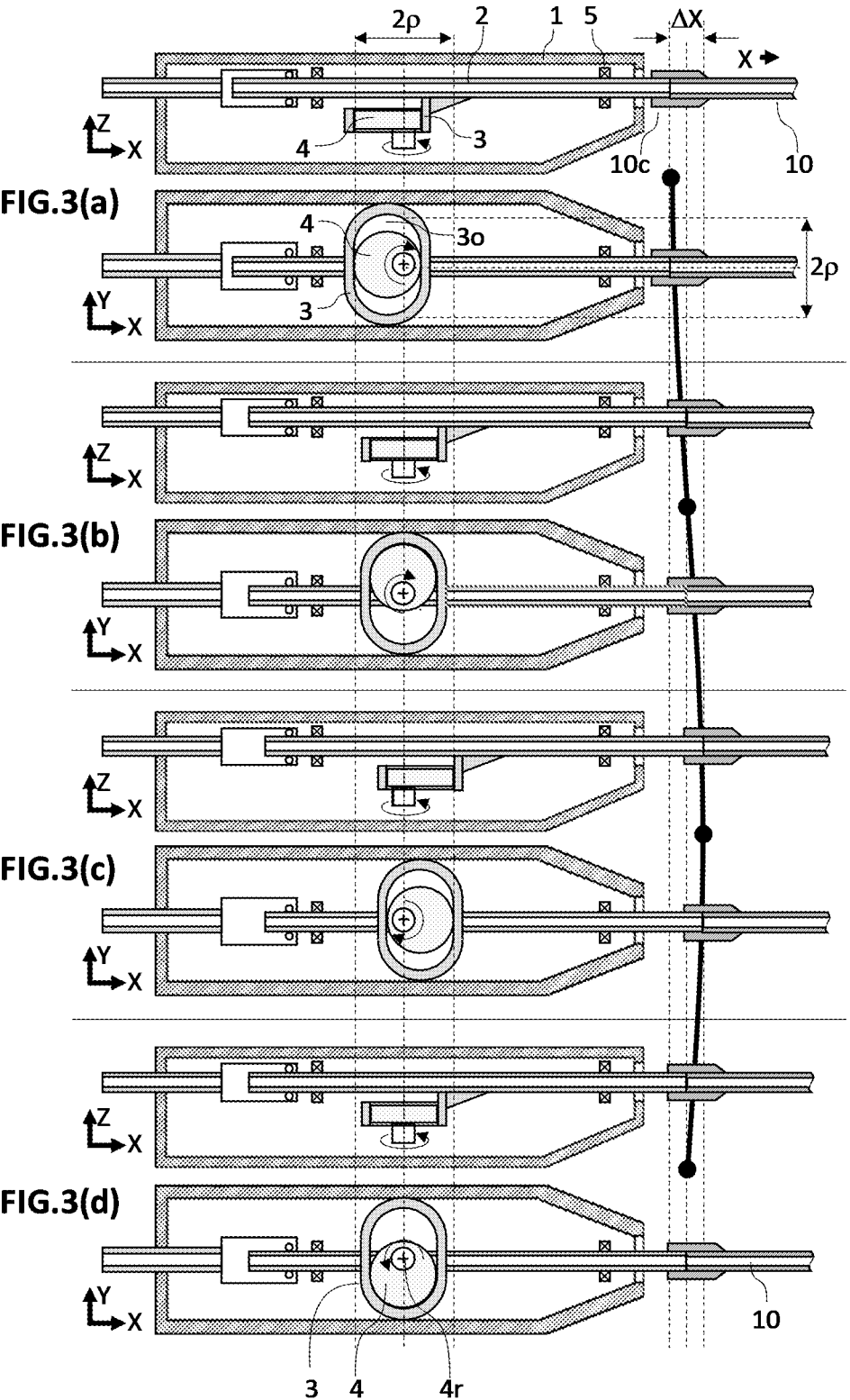
FIG. 3: shows top cut views and side cut views of a liposuction device with the cannula tip at different positions of the reciprocating movement thereof.

FIG. 1(a) shows in a first embodiment, a sealing component comprising a sheath (9s) made of a flexible material is sealed to or is integral with the hollow tube (2) and the outlet tube (20). The flexible material preferably is an elastomeric material or is a continuation of the hollow tube (2) and outlet tube (20), with thinner walls, rendering it flexible enough for absorbing the oscillations of the hollow tube. FIG. 1(d) shows in a second embodiment of sealing component comprising a bellow (9b) sealed to or integral with the hollow tube (2) and the outlet tube (20). In a third embodiment illustrated in FIG. 1(c), the sealing element comprises a chamber (9c) rigidly fixed relative to the outlet tube (20) and comprising dynamic sealing elements sealing an interface between the hollow tube (2) and a wall of the chamber (9c) during the back and forth translation of the hollow tube (2) relative to the housing.

Kit-of-Parts

The components configured for being coupled to one another to form an assembly for carrying out a liposuction operation are illustrated in FIGS. 4(a) to 4(d). They include a powered handpiece as discussed supra, including the hollow tube (2). A hollow cannula (10) comprises a lumen and has a coupling end configured for being coupled to the inlet end (2i) of the hollow tube (2), and a free end provided with openings giving access to the lumen of the cannula. As discussed supra, the motor (50) is mechanically coupled to the cam (4) for driving the rotation of the cam (4) about the rotation axle (4r). A vacuum pump (30) is configured for being coupled via a flexible tube (20t) in fluid communication with the outlet end (2o) of the hollow tube (2), preferably via the distal end (20d) of the outlet tube (20). The vacuum pump is configured for creating a vacuum in the lumen of the cannula (10) sufficient for drawing adipose tissue out of a location of a body. A collecting vessel (40) is configured for collecting adipose tissue extracted through the cannula (10) and for being sealingly coupled to the vacuum pump (30). The collecting vessel (40) includes an opening for receiving a downstream end of the flexible tube (20t). Collecting vessels of various types are known and available on the market.

As discussed supra, the motor (50) can be an electric, a hydraulic or a pneumatic motor and is preferably separate from the housing as illustrated in FIGS. 4(a) and 4(d). A separate motor can be directly or indirectly mechanically coupled to the cam (4) via a cable (50c) configured for transmitting a rotational torque for driving the rotation of the cam (4) about the rotation axle (4r).

Medical Device

A medical device for removing tissues from a body according to the present invention comprises the following components. A powered handpiece as described supra includes the hollow tube (2). A hollow cannula (10) extending between a coupled end and a free end, the coupled end is fixed to the inlet end (2i) of the hollow tube (2), such that the hollow cannula extends along the longitudinal axis (X) with the free end being located outside the powered handpiece. The cannula is fixed to the inlet end (2i) of the hollow tube by a connector (10c), which can be a separate connector, or can be integral with either the cannula or the hollow tube. The connector (10c) can be a bayonet, a thread, a snap fit, or any The motor (50) is coupled to the rotating axle (4r) of the cam (4) such as to drive the rotation thereof about the rotation axle (4r) and thus driving the back-and-forth translation of both hollow tube (2) and hollow cannula (10) along the longitudinal axis (X). As discussed supra, the motor can be separate from the housing or reversibly coupled thereto. The present medical device is particularly suited for liposuction of adipose tissue, wherein the cannula is preferably a single wall cannula comprising no second cannula enclosed in or enclosing the cannula, which is static relative to the cannula (10).

In a preferred embodiment, the medical device is configured for imparting a nutational movement to the free end of the hollow cannula when the hollow tube (2) translates back-and-forth along the longitudinal axis (Z). A nutation movement is defined as a movement comprising an orbital component about the longitudinal axis (X) and a translation component according to the longitudinal axis (X) of the cannula. The translation component preferably has an amplitude (i.e., end-to-end distance ran by the inlet of the cannula during one stroke in one direction along the longitudinal axis, X) of preferably less than 10 mm, and preferably greater than 1 mm. More preferably the amplitude of the translation component is comprised between 2 and 9 mm, more preferably between 5 and 8 mm. For a circular cam (4) of diameter, 2R=W, the amplitude of the reciprocal translation component of the nutational movement is 2 δR, wherein δR<R, is the offset of the rotation axle (4r) relative to the centre of the circular cam. The major diameter of the elliptical orbital component, followed by the cannula's tip when orbiting about the longitudinal axis, X, is preferably comprised between 1 and 20 mm, more preferably between 2 and 10 mm, more preferably between 5 and 8 mm. The characteristics of the vibrational movement of the tip of the cannula can be controlled by a combination of at least the following parameters:

The characteristics of the vibrational movement of the tip of the cannula can be controlled by a combination of at least the following parameters.

- The bending moment of the cannula (10), dependent on the length, diameter, cross-sectional geometry, wall thickness and material of the cannula,
- The smoothness, amplitude and frequency of the reciprocal translation along the longitudinal axis of the hollow tube, which must avoid shocks at the end of each stroke, which would disrupt the conditions for an orbital component of the vibrational movement of the cannula's tip. The present mechanism of a cam and a ring can provide a very smooth reciprocal movement, in particular if a circular cam of diameter 2R=W is used.
- A slight oscillation of the ring (3) and hollow tube (2) along the first transverse axis (Y) can trigger an orbital component to the free end of the cannula (10). This can be created by designing the reciprocal mechanism such as the largest radius of rotation, ρ, of the cam is slightly larger than the length, L, of the ring opening (3o) ((ρ−L)>0), or by slightly offsetting the rotation axle (4r) from a centre of the length, L, of the ring opening. The oscillation must be very small and the magnitude (ρ−L) or the offset should not exceed 3%, of the length, L, of the ring opening, preferably not exceed 1% of L.
- The clearance of the cannula (10) at an inlet end of the handpiece, which can control the extent the vibrational component of the cannula movement can develop in the radial direction,
- The mechanical pressure applied on surfaces of the cannula, e.g., by surrounding tissues when introduced into a body part (note that the parameters discussed supra refer to an unconstrained cannula, apart from its fixing point to the hollow tube (2)).

The same handpiece can also be used for a medical device configured for cutting tissue to be extracted. This can be achieved by coupling a specific cannula to the powered handpiece described supra. The specific cannula comprises an outer cannula fixed relative to the housing, and an inner cannula (10) enclosed in the outer cannula and fixed to the inlet end (2i) of the hollow tube (2) configured for reciprocating along the longitudinal axis (X).relative to the outer cannula.

The powered handpiece of the present invention provides a low-cost, low-weight, reliable solution for driving a reciprocal movement to a cannula (10). The cannula can even follow a nutational movement, which is known in the art to be advantageous for liposuction operations. The powered handpiece can be disposable, thus avoiding having to sterilize it after use. By using compatible materials, preferably of a same thermoplastic polymeric family, the powered handpiece as a whole can easily be recycled, without having to dismantle it first. By dissociating the motor (50) from the handpiece, the production costs are greatly reduced and, if separate from the handpiece, allows the weight of the handpiece to be reduced substantially.

| REF | DESCRIPTION |
| --- | --- |
| 1 | Housing of the powered handpiece |
| 2 | Hollow tube |
| 2i | Inlet of the hollow tube |

-continued

| REF | DESCRIPTION |
|---|---|
| 2o | Outlet of the hollow tube |
| 3 | Ring |
| 3o | Opening of the ring |
| 4 | Cam |
| 4r | Rotational axle of cam |
| 5 | Bearings for the hollow tube |
| 6 | First gear |
| 7 | Second gear |
| 7r | Rotational axle of second gear |
| 7s | Metal swaging tube |
| 7w | Worm gear |
| 9b | Bellow |
| 9c | Chamber |
| 9s | Sheath |
| 10 | Cannula |
| 10c | Connector between cannula and hollow tube |
| 20 | Outlet tube |
| 20d | Distal end of outlet tube |
| 20p | Proximal end of outlet tube |
| 20t | Flexible tube |
| 30 | Vacuum pump |
| 40 | Collecting vessel |
| 50 | Motor |
| 50c | Cable |
| 50m | Injection moulding mould for second gear |
| 50j | Joining portion between cable 50c and axle of cam 4r or of second gear 7a |
| C | Centroid of cam |
| L | Length of ring opening along Y |
| W | Width of ring opening along X |
| R | Radius of a circular cam |
| X | Longitudinal axis |
| Y | First transverse axis |
| Z | Second transverse axis |
| δP | Offset distance of axle to centroid of cam |
| ΔX | Amplitude of the reciprocating movement of the cannula tip |
| θ | rotation angle of cam |
| ρ | Largest radius of rotation of cam |

The invention claimed is:

1. A powered handpiece for imparting to a cannula of a medical device a reciprocal movement of amplitude (Δx) along a longitudinal axis (X), the powered handpiece comprising a housing (1) at least partially enclosing, (a) a hollow tube (2) extending along the longitudinal axis (X) between an inlet end (2i) and an outlet end (2o), configured for translating back and forth along the longitudinal axis (X) by a distance (ΔX) relative to the housing (1), the inlet end (2i) being configured for coaxially coupling the hollow tube (2) to a hollow cannula (10), (b) a ring (3) rigidly coupled to the hollow tube (2) and comprising an opening (3o) defined on a plane (X, Y), having a length, L, measured along a first transverse axis (Y) and a width, W, measured along the longitudinal axis (X), wherein Y⊥X, (c) a cam (4) mounted on a rotation axle (4r) parallel to a second transverse axis (Z) normal to the plane (X, Y) (i.e., X⊥Y⊥Z), offset from a centroid (C) of the cam on the plane (X, Y) by a distance (δR), and set at a fixed position relative to the housing (1), the cam being engaged in the opening (3o), wherein upon rotation about the rotation axle, the cam is configured for rotating within the ring and defining a largest radius of rotation (ρ) defined on the plane (X, Y), and wherein the largest radius of rotation (ρ) is not more than half the length, L, of the opening (ρ<½ L) and is larger than the width, W, of the opening, wherein the rotation of the cam (4) engaged in the opening (3o) of the ring (3) drives a reciprocal translation of the hollow tube (2) back and forth along the longitudinal axis (X) by the distance (ΔX) relative to the housing (1), and (d) a transmission system for transforming a rotation about a first rotation axis transverse to the second longitudinal axis (Z) driven by a motor (50) into a rotation about a second rotation axis parallel to the second transverse axis (Z) driving the rotation of the cam about the rotation axle (4r).

2. The powered handpiece according to claim 1, wherein the transmission system is selected among, skew gears comprising a first gear (6) rigidly mounted on the rotation axle (4r), and a second gear (7) configured for rotating about the first rotation axis and mechanically interacting with the first gear for driving the rotation of the first gear about the rotation axle (4r), or the first gear (6) engaged with a worm gear rotating about the first rotation axis, or a cardan joint.

3. The powered handpiece according to claim 2, wherein the cardan joint is present and is a homokinetic joint.

4. The powered handpiece according to claim 2, wherein the cardan joint is present and is a double-cardan joint.

5. The powered handpiece according to claim 1, comprising,
an outlet tube (20) rigidly fixed to the housing (1), positioned coaxially to the hollow tube (2), with a proximal end (20p) facing without contacting the outlet end (2o) of the hollow tube (2), and with a distal end (20d) extending out of the housing, and
a sealing component (9b, 9c, 9s) sealing from an outer atmosphere a space comprised between the outlet end (2o) of the hollow tube (2) and the proximal end (20p) of the outlet tube (20), allowing for the back and forth translation of the hollow tube (2) relative to the housing (1) and to the outlet tube (20).

6. The powered handpiece according to claim 5, wherein the sealing component (9b, 9c, 9s) is selected among,
a chamber (9c) rigidly fixed relative to the outlet tube (20) and comprising dynamic sealing elements sealing an interface between the hollow tube (2) and a wall of the chamber (9c) during the back and forth translation of the hollow tube (2) relative to the housing (1)
a bellow (9b) sealed to or integral with the hollow tube (2) and the outlet tube (20), or
a sheath (9s) made of a flexible material sealed to or integral with the hollow tube (2) and the outlet tube (20).

7. The powered handpiece according to claim 6, wherein the flexible material is an elastomeric material.

8. The powered handpiece according to claim 1, comprising at least one component of the powered handpiece, which is degraded at a temperature of more than 60° C. such that the powered handpiece cannot be used after a sterilization operation at a temperature above 60° C.

9. A kit of parts for liposuction of adipose tissue, said kit of parts comprising:
(a) a powered handpiece according to claim 1,
(b) a hollow cannula (10) comprising a lumen and having a coupling end configured for being coupled to the inlet end (2i) of the hollow tube (2), and a free end,
(c) a motor (50) mechanically coupled to the cam (4) for driving the rotation of the cam (4) about the rotation axle (4r),
(d) a vacuum pump (30) configured for being coupled via a flexible tube (20t) in fluid communication with the outlet end (2o) of the hollow tube (2), for creating a vacuum in the lumen of the cannula (10) sufficient for drawing adipose tissue out of a location of a body
(e) a collecting vessel (40) configured for collecting adipose tissue extracted through the cannula (10) and for being sealingly coupled to the vacuum pump (30) and including an opening for receiving a downstream end of the flexible tube (20t).

10. The kit of parts according to claim 9, wherein the motor (50) is separate from the housing and is directly or indirectly mechanically coupled to the cam (4) via a cable (50c) configured for transmitting a rotational torque for driving the rotation of the cam (4) about the rotation axle (4r).

11. The kit of parts according to claim 9, wherein the motor (50) is an electric motor, a pneumatic motor, or a hydraulic motor.

12. A medical device for removing tissues from a body comprising:
   a powered handpiece according to claim 1,
   a hollow cannula (10) extending between a coupled end and a free end, the coupled end being fixed to the inlet end (2i) of the hollow tube (2), such that the hollow cannula extends along the longitudinal axis (X) with the free end being located outside the powered handpiece, and
   a motor (50) configured for rotating the cam (4) about the rotation axle (4r) and thus driving the back-and-forth translation of both hollow tube (2) and hollow cannula (10) along the longitudinal axis (X).

13. The medical device according to claim 12, wherein the medical device is a device for liposuction.

14. The medical device according to claim 13, configured for imparting a nutational movement to the free end of the hollow cannula when the hollow tube (2) translates back-and-forth along the longitudinal axis (Z).

15. The medical device according to claim 12, comprising an outer cannula fixed relative to the housing, and wherein the cannula (10) is an inner cannula enclosed in the outer cannula and configured for reciprocating along the longitudinal axis (X), relative to the outer cannula.

16. The medical device according to claim 12, wherein the motor (50) is separate from the housing and is directly or indirectly mechanically coupled to the cam (4) via a cable (50c) configured for transmitting a rotational torque for driving the rotation of the cam (4) about the rotation axle (4r).

17. The powered handpiece according to claim 1, wherein the first rotation axis is parallel to the longitudinal axis (X).

* * * * *